United States Patent [19]
Probst et al.

[11] Patent Number: 4,760,205
[45] Date of Patent: Jul. 26, 1988

[54] 2-IODO-PERFLUORO-2-METHYLALKANES, PROCESSES FOR THEIR PREPARATION AND THEIR USE

[75] Inventors: Anton Probst; Klaus Raab, both of Burgkirchen; Konrad von Werner, Halsbach, all of Fed. Rep. of Germany

[73] Assignee: Hoechst Aktiengesellschaft, Frankfurt am Main, Fed. Rep. of Germany

[21] Appl. No.: 948,030

[22] Filed: Dec. 31, 1986

[30] Foreign Application Priority Data

Jan. 4, 1986 [DE] Fed. Rep. of Germany ....... 3600108

[51] Int. Cl.[4] .................. C07C 19/07; C07C 17/04
[52] U.S. Cl. .................. 570/137; 570/161; 570/174
[58] Field of Search ........................... 570/137

[56] References Cited

U.S. PATENT DOCUMENTS 3,008,966  11/1961  Hauptschein et al. ............. 570/137
3,377,390  4/1968   Rondestredt ...................... 570/137

FOREIGN PATENT DOCUMENTS 687714  6/1964  Canada ............................ 570/137
61104   6/1974  Japan ............................. 570/137
61103   6/1974  Japan ............................. 570/137
23333   2/1985  Japan ............................. 570/137

OTHER PUBLICATIONS

Seel, F. et al., Chem. Abs., 60:15407a, abstracting Z. Anorg. Allgem. Chem. 327, 28–31, (1964).
Mochalina, E. P. et al., Chem. Abs. 66:45901y, (1967), abstracting Dokl. Akad. Nauk SSSR 169, 1346–9, (1966).
Hauptschein, M. et al., J. Amer. Chem. Soc. 80, 842–845, (1958).
Kolta, G. et al., J. Fluorine Chem., 14, 331–337, (1979).
Ishikawa, M. et al., Chem. Lett., 1980, 1089–1090.

Primary Examiner—J. E. Evans

[57] ABSTRACT

New processes for the preparation of 2-iodo-perfluoro-2-methyl-butane and the corresponding -pentane are described. In one process, perfluoro-2-methyl-2-butene or the corresponding -pentene is reacted in an amount of at least 5 mol with a mixture of 2 mol of iodine and 1 mol of iodine pentafluoride in the presence of more than 1 mol of at least one fluoride of a metal of group I of the periodic table of the elements under the autogenous pressure of the reaction mixture at 170° to 220° C. for 2 to 30 hours. In another process, the same perfluoroolefins are reacted, as the starting substances, with iodine and an alkali metal fluoride in the presence of at least 1 mol of a soluble silver salt per mole of the perfluorinated olefin at 20° to 100° C. for 0.5 to 10 hours. After working up by distillation, the pure iodoperfluoroalkanes are obtained. They are suitable for numerous reactions, but in particular as a packing for lasers.

1 Claim, No Drawings

2-IODO-PERFLUORO-2-METHYLALKANES, PROCESSES FOR THEIR PREPARATION AND THEIR USE

The invention relates to novel 2-iodo-perfluoro-2-methylalkanes, their preparation and their use in accordance with the subsequent patent claims.

Only 2-iodo-perfluoro-2-methylpropane, the corresponding alkane with the lowest molecular weight, is known to date. It is a solid highly volatile substance of melting point 81° C. and can be prepared, for example, in accordance with the method of J. A. Young and Th. M. Reed, J. Org. Chem. 32 (1967), page 1682, right-hand column, 2nd paragraph, by catalyzed addition of the elements of iodine monofluoride onto highly toxic perfluoroisobutylene at 130° C. in the course of 60 hours. A mixture of 2 mol of iodine and 1 mol of Iod pentafluoride is used by M. Hauptschein; A. H. Fainberg and M. Braid, J. Am. Chem. Soc. 80 (1958), page 842 et seq. as the source for iodine monofluoride. As the subsequent comparison experiments A to D show, no iodine fluoride can be added onto perfluoro-2-methyl-2-butene or perfluoro-2-methyl-2-pentene by this method, even if metal fluorides, such as antimony(V) fluoride or cobalt(III) fluoride, are employed in substantial amounts as the catalyst. Even if only 1 mol of potassium fluoride is used per mol of iodine pentafluoride employed, only traces of the addition compound of iodine fluoride are obtained.

2-Iodo-perfluoro-2-methylpropane can furthermore be obtained in a good yield in accordance with the method of E. P. Mochalina; B. L. Dyatkin; I. V. Galakhor and I. L. Knunyants; Dokl. Akad. Nauk. SSSR 169 (6) pages 1346–1349 (1966), abstracted in C.A. 66 (1967) No. 45901 Y, by heating perfluoroisobutylene with iodine, potassium fluoride and nitrobenzene at 170° to 180° C. in a steel autoclave for 10 hours. As the subsequent comparison experiment E shows, this process is likewise unsuitable for preparing 2-iodo-perfluoro-2-methyl-butane or the corresponding pentane by addition of iodine fluoride onto the corresponding perfluorinated olefins. According to comparison experiment F, this also fails to take place if the nitrobenzene used as the solvent is omitted.

A process has now been found for preparing 2-iodo-perfluoro-2-methyl-butane or the corresponding pentane. The invention accordingly relates to compounds of the formula

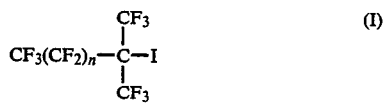

in which n denotes 1 or 2, and a process for the preparation of compounds of the formula (I) by reaction of perfluorinated, branched-chain olefins with a mixture of iodine and iodine pentafluoride in a molar ratio of 2:1 at elevated temperature under the autogenous pressure of the reaction mixture or a pressure above this pressure, which comprises using perfluoro-2-methyl-2-butene or perfluoro-2-methyl-2-pentene as the perfluorinated branched-chain olefin in an amount of at least 5 mol per mol of iodine pentafluoride used, and carrying out the reaction in the presence of more than 1 mol of at least one fluoride of a metal of group I of the periodic table of the elements per mol of iodine pentafluoride used.

Perfluoro-2-methyl-2-butene can be obtained, for example, by isomerization of perfluoro-2-methyl-3-butene, which is prepared in accordance with the method of R. N. Haszeldine et al., J. Chem. Soc. Perkin I/1973, page 574. The isomerization is described by R. N. Haszeldine et al., Chem. Commun. 1970, page 1444 et seq. The preparation of perfluoro-2-methyl-2-pentene is also described there. Each of the two compounds is employed in an amount of at least 5 mol per mol of iodine pentafluoride ($IF_5$) used. If less than 5 mol of the compounds mentioned is used per mol of $IF_5$, the 2-iodo-perfluoro-2-methyl-alkanes of the formula (I) are obtained only in smaller yields. More than 5 mol of perfluoro-2-methyl-2-butene or the corresponding -pentene per mol of $IF_5$ can be employed without disadvantage, since these starting products can easily be separated off from the end products of the formula (I) by distillation during the working up which takes place after the reaction, because the boiling points of the perfluoroolefins are considerably lower than those of the iodides. 10 mol of perfluoroolefins per mol of $IF_5$ will not be exceeded merely for economic reasons, so that an unnecessarily high amount of the unreacted starting products used does not have to be recovered. The reaction is furthermore carried out in the presence of more than 1 mol of at least one fluoride of a metal of group I of the periodic table of the elements per mol of $IF_5$ used. Examples of suitable fluorides are sodium fluoride, lithium fluoride, rubidium fluoride, copper(I) fluoride and silver fluoride. Systems which form the fluorides mentioned, for example a mixture of finely divided metallic copper and copper(II) fluoride, are also suitable. Particularly good results are obtained with potassium fluoride and cesium fluoride.

The fluorides mentioned can be activated by known processes, for example with sulfur dioxide, as described by F. Seel and H. D. Görlitz; Z. f. Anorg. Allg. Chem. 327 (1964) page 32, or by freeze drying, see N. Tshikawa; T. Kitazume and M. Nakabayashi, Chem. Lett. 1980, page 1089, and furthermore also by vacuum drying or with the aid of perfluoroacetone, as described by G. A. Kolta; G. Webb and J. M. Winfield, J. Fluorine Chem. 14 (1979), page 331. However, particular activation is in general not necessary.

Mixtures of various metal fluorides of group I of the periodic table of the elements can also be used.

More than 1 mol of the fluorides described in the preceding paragraph is employed per mol of $IF_5$. If the metal fluoride is not used in a molar excess, only small amounts of the compounds of the formula (I) are obtained, as the subsequent comparison experiment B shows. The upper limit of the amount of metal fluoride used is essentially determined by economic considerations, no further additional effect being found with more than 5 mol of metal fluoride per mol of $IF_5$, and the reaction of the perfluoroolefin with the mixture of iodine and $IF_5$ is preferably carried out in the presence of 1.1 to 4 mol of metal fluoride per mol of $IF_5$ used.

The reaction temperature in the process according to the invention described in more detail above should preferably be between 170° and 220° C. Below 170° C., the rate of reaction is distinctly reduced, so that unnecessarily long reaction times are required, and above 220° C. the formation of undesirable by-products is found to an increasing degree. Particularly good results are obtained if the reaction temperature is kept between 180° and 210° C.

The duration of the reaction depends on the reaction temperature chosen, and is advantageously between 2 and 12 hours at temperatures above 200° C.; at temperatures in the range from 170° C. it can be up to 30 hours, and good results are achieved with a duration of the reaction of 7 to 15 hours.

The reaction is carried out under the autogenous pressure of the reaction mixture, in general between 2.2 and 2.7 MPa, depending on the temperature, and higher pressures such as may arise, for example, by the presence or addition of inert gases, for example argon or nitrogen, do not have an adverse influence on the process according to the invention. During the reaction, the contents of the reaction vessel are advantageously kept continuously in motion, for example by stirring or shaking. All the reagents used must be completely anhydrous, and the action of water vapor must also be excluded during charging of the reaction vessel by using a dry inert gas protective atmosphere. Autoclaves of chromium-nickel steel which is resistant to chemicals are suitable as the reaction vessel.

At the end of the chosen reaction time, the reaction vessel is cooled to room temperature and slowly let down and the liquid and solid constituents which remain are stirred into a 1 to 20% strength by weight aqueous solution, advantageously cooled to $-3°$ to $+6°$ C., of an alkali metal hydroxide, for example sodium hydroxide. 2 phases are thereby formed, and the organic phase is separated off, washed with water which is as cold as possible, subsequently dried with a suitable solid drying agent, for example magnesium sulfate, and subjected to fractional distillation under normal pressure. If perfluoro-2-methyl-2-butene has been used as the starting substance, unreacted portions of this compound pass over at about 27° C. and are collected in a receiver cooled with cooling brine. The main fraction consists of highly pure 2-iodoperfluoro-2-methyl-butane and is distilled off as a violet liquid at 89° to 90° C. If perfluoro-2-methyl-2-pentene has been used as the starting substance, the unreacted olefin passes over at about 51° C. The 2-iodo-perfluoro-2-methylpentane is likewise distilled as a highly pure violet liquid at 115° C.

Caution! Like the known compound 2-iodo-perfluoro-2-methyl-propane, the compounds of the formula (I) obtained in the process according to the invention are also highly toxic substances which are considerably volatile, and the perfluorinated olefins used are also toxic, which is why the entire operation for the preparation, according to the invention, of the compounds of the formula (I) is to be carried out with appropriate safety measures, in particular removal by suction and destruction of escaping gases.

The invention furthermore relates to a process for the preparation of compounds of the formula (I) by reaction of perfluorinated branched olefins with iodine and an alkali metal fluoride in the presence of an aprotic solvent, if appropriate at elevated temperature, which comprises using perfluoro-2-methyl-2-butene or perfluoro-2-methyl-2-pentene as the perfluorinated branched-chain olefin and carrying out the reaction in the presence of at least 1 mol of a soluble silver salt per mol of perfluorinated olefin.

Various molar ratios of iodine and alkali metal fluoride can be employed, and a molar excess of the alkali metal fluoride is advantageously used. Because of the favorable price, sodium fluoride or potassium fluoride is preferably used. If the soluble silver salt is silver fluoride, the use of the alkali metal fluoride can advantageously be dispensed with.

Examples of suitable aprotic solvents are nitriles, for example acetonitrile; ethers, for example diethylene glycol dimethyl ether or diethylene glycol diethyl ether; acid amides, for example dimethylformamide or N-methylacetamide, and nitro compounds, for example nitrobenzene.

The proportion of perfluoro-2-methyl-2-butene or perfluoro-2-methyl-2-pentene used in relation to the iodine and alkali metal fluoride used is not critical. Since, as already mentioned above, the perfluorinated olefins used as the starting substance can easily be separated from the compounds of the formula (I) by distillation, an excess of the fluorinated olefins can be used, but equimolar amounts, based on the iodine and alkali metal fluoride, are advantageously employed. The perfluorinated olefin can also be used in less than the equimolar amount.

The reaction is carried out in the presence of at least 1 mol of a soluble silver salt per mol of perfluorinated olefin. If less than 1 mol of silver salt is employed, a considerable reduction in the yield of compounds of the formula (I) is found. The upper limit of the amount of silver salt used is determined only by economic considerations, and in general 1 to 2 mol of silver salt per mol of perfluorinated olefin is entirely adequate.

Soluble silver salts are to be understood as those which are soluble to the extent of at least 5 g per $dm^3$ in acetonitrile at 20° C. Examples of suitable silver salts are the carboxylates of carboxylic acids which do not have a reducing action and do not react with iodine under the reaction conditions, such as, for example, acetic acid, and furthermore silver tetrafluoborate or hexafluorophosphate, silver sulfate or silver nitrite. Silver nitrate, silver trifluoroacetate and silver fluoride are preferred because of their particularly advantageous effect. Silver fluoride also has the further advantage that the use of an alkali metal fluoride becomes unnecessary.

The reaction described in the immediately preceding sections is preferably carried out at 20° to 100° C. Below 20° C., the duration of the reaction is in general increased unnecessarily, and above 100° C. unnecessarily expensive equipment is required because the autogenous pressure of the reaction mixture increases as the temperature increases, and also the formation of undesirable hydroperfluoroalkane increases. As a rule, it is sufficient to carry out the reaction under atmospheric pressure, reflux conditions advantageously being chosen.

The process described above can also be carried out without an aprotic solvent at temperatures above 100° C., but distinctly poorer yields are found here.

The reaction must be carried out with substantially anhydrous starting substances, and during the reaction a dry protective gas atmosphere, for example argon or nitrogen, is advantageously used.

The reaction is as a rule concluded 0.5 to 20 hours after the reaction temperature has been established and maintained. A duration of reaction of 1 to 5 hours is preferably chosen.

When the reaction has ended, the solid constituents of the reaction mixture are advantageously separated off by filtration, for example on a frit, applying a slight increased pressure, and are washed with a small amount of the aprotic solvent used. Water of 0° to 10° C. is added to the filtrate and the organic phase formed is separated off and extracted by shaking again with cold water. Finally, the organic phase is rendered as anhydrous as possible with a suitable solid drying agent, for example magnesium sulfate, and subsequently subjected to fractional distillation. The distillation temperatures of the individual fractions have already been described above. The compounds of the formula (I) are likewise obtained as highly pure violet liquids.

Caution! As already mentioned above, thorough safety measures are also required for the processes just described, because of the toxicity of the starting substances employed and the end products obtained.

The silver iodide formed can easily be isolated from the filter residue of the reaction just mentioned by washing with water. The silver is advantageously deposited from this by reduction, for example with hydrazine or another suitable reducing agent, and the iodine is recovered from the remaining portion by subsequent careful oxidation, for example with hydrogen peroxide.

The unreacted perfluoroolefin separated off as a low-boiling fraction during the distillation can be reused without further purification.

The compounds of the formula (I) prepared according to the invention are highly reactive and can be added onto olefins, such as, for example, ethene or tetrafluoroethene, or onto alkynes, such as, for example, propyne or phenylacetylene, for example at 100° to 150° C. without a catalyst. A number of products with a good surface-active effect can be prepared by customary methods from the addition compounds, which are accessible in high yields. The compounds of the formula (I) are furthermore particularly suitable for use in iodine photo dissociation lasers, in particular where excitation is by sunlight (solar-pumped lasers). Compounds which have an ultraviolet absorption maximum at 285 nm or more and the minimum possible tendency to form a dimer after removal of the iodine by dissociation are desirable for the use last mentioned. The latter property is achieved if the iodine is bonded to a tertiary carbon atom of a perfluorinated alkane. However, the toxicity of the products is thereby increased, so that compounds of relatively low volatility are generally of advantage. This is the case with the products of the formula (I), compared with the known compound 2-iodo-perfluoromethyl-propane. The compounds of the formula (I) furthermore exhibit particularly advantageous ultraviolet absorption maxima, as shown by the following Table I.

TABLE I

| UV data of iodo-perfluoroalkanes | | |
|---|---|---|
| Compound | $\lambda_{max}$ (nm) | $\epsilon$ |
| $CF_3-(CF_2)_5-I$ | 273,0 | 278 |
| $CF_3-(CF_2)_3-\underset{\underset{\mid}{CF_3}}{\overset{\overset{CF_3}{\mid}}{C}}-I$ | 282,0 | 210 |
| $(CF_3)_2CF-CF_2-\underset{}{\overset{\overset{CF_3}{\mid}}{C}F}-I$ | 281,9 | 200 |
| $CF_3-\underset{\underset{\mid}{CF_3}}{\overset{\overset{CF_3}{\mid}}{C}}-I$ | 287,2 | 199 |

TABLE I-continued

| UV data of iodo-perfluoroalkanes | | |
|---|---|---|
| Compound | $\lambda_{max}$ (nm) | $\epsilon$ |
| $CF_3-CF_2-\underset{\underset{\mid}{CF_3}}{\overset{\overset{CF_3}{\mid}}{C}}-I$ (IIa) | 292,6 | 190 |
| $CF_3-(CF_2)_2-\underset{\underset{\mid}{CF_3}}{\overset{\overset{CF_3}{\mid}}{C}}-I$ (IIb) | 294,6 | 196 |

All measurements in n-hexane.
$\lambda_{max}$ = maximum of the absorption band
$\epsilon$ = molar extinction coefficient.

The following examples and comparison experiments are intended to illustrate the invention in more detail:

Preparation of 2-iodo-perfluoro-2-methyl-butane

Example 1

An autoclave of $V_2A^R$ steel with a capacity of 250 cm³ is charged with 5.8 g (0.1 mol) of potassium fluoride powder and heated at 200° C. in vacuo for 1 hour for complete drying. After cooling to room temperature, 11.1 g (0.05 mol) of iodine pentafluoride and 25.4 g (0.1 mol) of iodine are introduced into the autoclave under a dry argon atmosphere, the autoclave is cooled to −70° C. and evacuated and 62.5 g (0.25 mol) of perfluoro-2-methyl-2-butene are condensed in. The autoclave is heated to 185° C. in the course of 2 hours, with shaking, and is shaken at this temperature for 12 hours. After cooling to room temperature, the autoclave is slowly let down in an effective fume cupboard and the liquid contents of the autoclave are stirred into 100 ml of ice-cold 10% strength by weight aqueous sodium hydroxide solution. The organic phase is washed with ice-cold water, dried with a little magnesium sulfate and distilled under normal atmospheric pressure. 72.3 g of a violet liquid of boiling point 89° to 90° C. (73% yield, based on the perfluoro-2-methyl-2-butene employed) are obtained as the main runnings. According to its $^{19}F$ nuclear magnetic resonance spectrum, the product consists of 2-iodo-perfluoro-2-methyl-butane to the extent of at least 99.5%.

Example 2

A four-necked flask with a capacity of 250 cm³ and charged with 11.6 g (0.2 mol) of potassium fluoride is heated to 200° C. in vacuo, cooled to room temperature and equipped with a stirrer, thermometer and a dry ice condenser, on the top outlet of which is attached a drying tube filled with blue gel. 100 cm³ of pure anhydrous acetonitrile and 22.1 g (0.1 mol) of silver(I) trifluoroacetate are now added and the flask is closed with a septum cap. After the contents of the flask have been cooled to 10° C., 25.0 g (0.1 mol) of perfluoro-2-methyl-2-butene are injected into the flask through the septum with the aid of a cooled syringe. The mixture is stirred at room temperature for 1 hour and then at 30° C. for 30 minutes. After cooling to room temperature, 25.4 g (0.1 mol) of iodine are added. The mixture is now stirred first at room temperature for 1 hour and then under reflux for 3 hours and is subsequently cooled to room temperature. The solid portions (potassium fluoride, potassium trifluoroacetate and silver(I) iodide) are separated off on a frit by filtration under a slight increased pressure and are washed with a little acetonitrile. The filtrate is diluted with ice-water and the lower organic phase is separated off, extracted by shaking with cold water, separated off again and dried with a little magnesium sulfate. It is then subjected to fractional distillation. 31.4 g of product are obtained as the main runnings (79.3% yield, based on the perfluoro-2-methyl-2-butene). The purity corresponds to that of the product produced according to Example 1.

Preparation of 2-iodo-perfluoro-2-methyl-2-pentane

Example 3

120 g (0.4 mol) of perfluoro-2-methyl-2-pentene, 11.1 g (0.05 mol) of iodine pentafluoride, 25.4 g (0.15 mol) of iodine and 5.8 g (0.1 mol) of potassium fluoride are reacted and worked up as described in Example 1, with the difference that the reaction is carried out at 190° C. for 15 hours. Fractional distillation under normal pressure gives 99.7 g of a violet liquid of boiling point 115° C. The yield is 89.4%, based on the iodine pentafluoride, and according to investigation by gas chromatography, the product consists of 2-iodo-perfluoro-2-methyl-2-pentane to the extent of 99.5%. At 22° C., the density of the product is 2.14 g/cm$^3$ and the vapor pressure is 2800 Pa.

Example 4

0.3 mol of perfluoro-2-methyl-2-pentene, 0.05 mol of iodine pentafluoride, 0.1 mol of iodine and 0.1 mol of cesium fluoride are reacted and worked up as described in Example 1, but with the difference that the reaction is carried out at 210° C. for 15 hours. 38.1 g of the product described in Example 3 are obtained. The yield is 34.1%, based on the iodine pentafluoride.

Example 5

30.0 g (0.1 mol) of perfluoro-2-methyl-2-pentene, 22.1 g (0.1 mol) of silver(I) trifluoroacetate and 11.6 g (0.2 mol) of dry potassium fluoride are stirred in 100 cm$^3$ of anhydrous pure acetonitrile at 30° C. for 1 hour. After cooling to room temperature and addition of 25.4 g (0.1 mol) of iodine, the mixture is stirred at room temperature for 1 hour and then under reflux for 2.5 hours. Working up is carried out as described in Example 2, but the fractional distillation is dispensed with, since according to the $^{19}$F nuclear magnetic resonance spectrum, the washed crude product already consists of pure 2-iodo-perfluoro-2-methyl-2-pentane. The yield is 42.4 g=95%, based on the perfluoro-2-methyl-2-pentene employed. 23.0 g of silver(I) iodide are obtained by washing the filter residue with water and drying (98% yield, based on the silver(I) trifluoroacetate employed).

Example 6

The procedure followed is as described in Example 5, but 17.0 g (0.1 mol) of silver(I) nitrate are employed instead of silver(I) trifluoroacetate. The yield of 2-iodo-perfluoro-2-methyl-2-pentane is 75%, based on the perfluoroolefin employed, and the yield of silver(I) iodide is 94%, based on the silver(I) nitrate employed.

Example 7

The procedure followed is as in Example 5, but 12.7 g (0.1 mol) of silver(I) fluoride are employed instead of silver(I) trifluoroacetate, the potassium fluoride is omitted and the reaction is carried out with the exclusion of light. The yield of 2-iodo-perfluoro-2-methyl-2-pentane is 94%, based on the perfluoroolefin employed, and the yield of silver(I) iodide is 98.5%, based on the silver(I) fluoride employed.

The nuclear magnetic resonance data of the known compound 2-iodo-perfluoro-2-methyl-propane and those of the two 2-iodo-perfluoro-alkanes prepared according to the invention are shown in the following Table II.

TABLE II

| Compound | $^{13}$C: Chemical shift and ($^{13}$C, $^{19}$F)Linkages | $^{19}$F: Chemical shift |
|---|---|---|
| ② CF$_3$—C(CF$_3$)(CF$_3$)—I ② | ① 37.09 ppm, Decet (30.5 Hz)<br>② 121.75 ppm, Quartet (290 Hz) | ② 14.45 ppm |
| ③ CF$_3$—CF$_2$—C(CF$_3$)(CF$_3$)—I ② ④ ① ② | ① 38.55 ppm, Septet (30.5 Hz) of Triplets (25.2 Hz)<br>② 122.78 ppm, Quartet (286.8 Hz)<br>③ 118.34 ppm, Quartet (288.4 Hz) of Triplets (35.3 Hz)<br>④ 113.02 ppm, Triplet (269 Hz) of Quartets (40.4 Hz) | ② 16.16 ppm<br>③ 0.19 ppm<br>④ −24.84 ppm |
| ③ CF$_3$—CF$_2$—CF$_2$—C(CF$_3$)(CF$_3$)—I ⑤ ④ ① ② | ① 38.90 ppm, Septet (30.8 Hz) of Triplets (24.6 Hz)<br>② 122.72 ppm, Quartet (286.5 Hz)<br>③ 118.61 ppm, Quartet (288.8 Hz) of Triplets (34.1 Hz)<br>④ 114.68 ppm, Triplet (269.2 Hz) of Triplets (34.0 Hz)<br>⑤ 109.78 ppm, Triplet (272.8 Hz) of Sextets (37.7 Hz) | ② 16.36 ppm<br>③ −3.06 ppm<br>④ −21.55 ppm<br>⑤ −43.30 ppm |

All measurements in CDCl$_3$
$^{13}$C—NMR: 50.323 MHz, tetramethylsilane as the internal standard
$^{19}$F—NMR: 75.393 MHz, trifluoroacetic acid as the external standard

Comparison Experiment A 0.05 mol of iodine pentafluoride and 0.1 mol of iodine are introduced into an autoclave of V$_2$A$^R$ steel with a capacity of 250 cm$^3$ under a dry argon atmosphere, the autoclave is cooled to −70° C. and evacuated and 0.3 mol of perfluoro-2-methyl-2-butene is condensed in.

The autoclave is heated to 190° C. in the course of 2 hours, with shaking, and is shaken at this temperature for 15 hours. The subsequent procedure is now as described in Example 1. The perfluoroolefin is largely retained during the fractional distillation. Evidently no 2-iodo-perfluoro-2-methyl-butane has formed.

Comparison Experiment B

The procedure followed is as described in Example 1, but only 0.05 mol of potassium fluoride is employed instead of 0.1 mol and 0.3 mol of perfluoro-2-methyl-2-butene is employed instead of 0.25 mol. The reaction temperature is adjusted to 200° C. and the reaction time is 15 hours. On working up, only traces of 2-iodo-perfluoro-2-methyl-butane are obtained.

Comparison Experiment C

The procedure followed is as in Comparison Experiment B, but 0.05 mol of antimony(V) fluoride is employed instead of 0.05 mol of potassium fluoride and the reaction temperature is 210° C. No 2-iodo-perfluoro-2-methyl-butane is obtained.

Comparison Experiment D

The procedure followed is as in Comparison Experiment B, but 0.1 mol of cobalt(III) fluoride is used instead of 0.05 mol of potassium fluoride. No 2-iodo-perfluoro-2-methyl-butane is obtained.

Comparison Experiment E 0.17 mol of perfluoro-2-methyl-2-pentene; 0.16 mol of iodine; 0.34 mol of potassium fluoride and 30 cm³ of nitrobenzene are reacted at 175° C. for 10 hours analogously to the method of E. P. Mochalina et al. Docl-Akad-Nauk SSSR 169 (6) pages 1346–1349 (1966). On working up, no 2-iodo-perfluoro-2-methyl-pentane is obtained.

Comparison Experiment F

The procedure followed is as in Comparison Experiment E, but no solvent (nitrobenzene) is used and the reaction is carried out at 200° C. for 15 hours. Here also, no 2-iodo-perfluoro-2-methyl-pentane is obtained.

We claim:

1. A compound of the formula

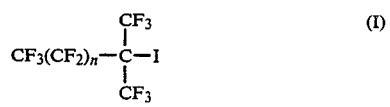

in which n denotes 1 or 2.